United States Patent
Kahn et al.

(10) Patent No.: US 10,610,146 B1
(45) Date of Patent: Apr. 7, 2020

(54) UTILIZING WEARABLE DEVICES IN AN INTERNET OF THINGS ENVIRONMENT

(71) Applicants: Philippe Richard Kahn, Santa Cruz, CA (US); Arthur Kinsolving, Santa Cruz, CA (US)

(72) Inventors: Philippe Richard Kahn, Santa Cruz, CA (US); Arthur Kinsolving, Santa Cruz, CA (US)

(73) Assignee: DP TECHNOLOGIES, INC., Scotts Valley, CA (US)

( * ) Notice: Subject to any disclaimer, the term of this patent is extended or adjusted under 35 U.S.C. 154(b) by 160 days.

(21) Appl. No.: 15/387,640

(22) Filed: Dec. 21, 2016

Related U.S. Application Data

(60) Provisional application No. 62/270,573, filed on Dec. 21, 2015.

(51) Int. Cl.
*A61B 5/18* (2006.01)
*G05D 1/00* (2006.01)
(Continued)

(52) U.S. Cl.
CPC ............... *A61B 5/18* (2013.01); *B60Q 9/00* (2013.01); *G05D 1/0016* (2013.01);
(Continued)

(58) Field of Classification Search
CPC ......... B60W 40/08; B60W 50/16; B60N 2/44; B60N 2/0244; B60N 2/02; B60N 2/919; B60K 28/066; B60K 28/06; B60K 28/02; G08B 23/00; G08B 21/06; G08B 13/14; G08B 1/08; G08B 13/1427; G08B 21/0219; G08B 21/0255; G08B 21/0275; G08B 25/08; G08B 5/36; G08B 6/00; G08B 21/0453; G08B 21/0202; A61B 5/4812; A61B 5/6801; A61B 5/6893; A61B 5/6898; A61B 5/18; A61B 5/00; A61B 5/6802; A61B 5/7455; A61B 5/746; A61B 5/02055; A61B 5/6838; A61B 5/747; A61B 5/1116; A61B 5/02438; A61B 5/1112; A61B 5/1118; A61B 5/0022; B60G 17/0195; B60G 17/015; A61M 21/00; A61M 21/02; G06K 19/0705; G06K 19/07762; G06K 19/0711; G06K 19/071; G06K 19/0707; G06K 19/072; H04L 67/12; H04L 12/2803; H04L 12/6418; H04L 67/125; G06F 1/163; G06F 19/3418; G06F 19/3481;
(Continued)

(56) References Cited

U.S. PATENT DOCUMENTS

| | | | | |
|---|---|---|---|---|
| 2012/0242481 A1* | 9/2012 | Gernandt | ............ | G06K 19/0705 340/539.13 |
| 2015/0188389 A1* | 7/2015 | Wan | .......................... | F03G 7/08 290/1 A |

(Continued)

*Primary Examiner* — Behrang Badii
(74) *Attorney, Agent, or Firm* — HIPLegal LLP; Judith Szepesi

(57) ABSTRACT

In one embodiment, the present system is designed to be a wearable garment, worn in a vehicle, such as a car. The wearable garment includes a plurality of sensors. These sensors may be used by a processor to identify precursor signs of dozing off. In one embodiment, the processor may be in the wearable garment. In another embodiment, the processor may be in a mobile device linked to the wearable garment.

18 Claims, 8 Drawing Sheets

(51) Int. Cl.
*B60Q 9/00* (2006.01)
*H04L 29/08* (2006.01)
*B60W 40/08* (2012.01)
*A61B 5/00* (2006.01)
*A61B 5/11* (2006.01)
*B60K 28/02* (2006.01)
*G08B 21/06* (2006.01)
*G16H 50/20* (2018.01)

(52) U.S. Cl.
CPC .............. *H04L 67/125* (2013.01); *A61B 5/00* (2013.01); *A61B 5/11* (2013.01); *A61B 5/6803* (2013.01); *B60K 28/02* (2013.01); *B60W 40/08* (2013.01); *G08B 21/06* (2013.01); *G16H 50/20* (2018.01)

(58) Field of Classification Search
CPC ....... H04W 4/029; H04W 4/80; H04W 12/08; B60Q 9/00; G05D 1/0016; B60R 16/037
See application file for complete search history.

(56) References Cited

U.S. PATENT DOCUMENTS

| | | | |
|---|---|---|---|
| 2015/0314681 A1* | 11/2015 | Riley, Sr. | B60W 50/16 340/576 |
| 2016/0039424 A1* | 2/2016 | Hong | B60W 40/08 701/2 |
| 2016/0066847 A1* | 3/2016 | Sales | A61B 3/112 600/324 |
| 2016/0128619 A1* | 5/2016 | Geller | A61B 5/6803 600/595 |
| 2016/0176409 A1* | 6/2016 | Kirsch | B60W 40/08 701/37 |
| 2016/0207454 A1* | 7/2016 | Cuddihy | B60Q 9/00 |
| 2016/0249815 A1* | 9/2016 | Freeman | H04W 4/029 600/483 |
| 2016/0308971 A1* | 10/2016 | Sweeney | H04L 67/12 |
| 2017/0153636 A1* | 6/2017 | Boesen | G06F 1/163 |
| 2017/0265798 A1* | 9/2017 | Sales | A61B 5/18 |
| 2018/0260064 A1* | 9/2018 | Chae | H04M 1/725 |

* cited by examiner

UTILIZING WEARABLE DEVICES IN AN INTERNET OF THINGS ENVIRONMENT

RELATED APPLICATIONS

The present applications claims priority to U.S. Provisional Application No. 62/270,573, filed on Dec. 21, 2015, and incorporates that application in its entirety by reference.

FIELD

The present invention relates to wearables, and more particularly to an interaction between wearables and the Internet of Things (IoT).

BACKGROUND

Wearables are clothing or other wearable items which include one or more sensors or other electronic features. Wearables include wrist bands, which are used to monitor a user's activities, as well as glasses including sensors, or chest straps or bras including sensor systems.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

In one embodiment, the present system is a wearable, which may be a garment such as a jacket or shirt. In one embodiment, the wearable may be worn in an Internet of Things (IoT) connected location, such as in a vehicle. The wearable includes a plurality of sensors. These sensors may be used by a processor to identify precursor signs of dozing off, when the user is driving.

In one embodiment, the processor may be integrated in the wearable garment. In another embodiment, the processor may be in a mobile device linked to the wearable garment. The mobile device may be a user cell phone, or part of the IoT environment. In one embodiment, processing may be split between one or more of the wearable garment, mobile device, a server, and the IoT environment, which may include local, remote, and cloud processing.

In one embodiment, the sensors include a temperature sensor, which enable the system to identify the user's body temperature as well as the ambient temperature. The system may, in one embodiment, adjust the temperature in a vehicle for ideal conditions, and to ensure that the user does not doze off.

In one embodiment, the wearable garment and the mobile device maintain a proximity connection, which enables each to warn if the other is left behind. Such a wearable garment, which in one embodiment is a jacket, is a useful indicator/sign-post of a user "physiological state" in a non invasive way. In addition to user motion data, body and external temperature differential and changes, as well as changes in elevation are informative.

In one embodiment, the mobile device, or the connected navigation system within a vehicle, may be to automatically redirect a user to a safe resting location, when the user is drowsy. This may be provided as an option if a change in the environment and/or an alert is insufficient to rouse the user from drowsiness.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1:
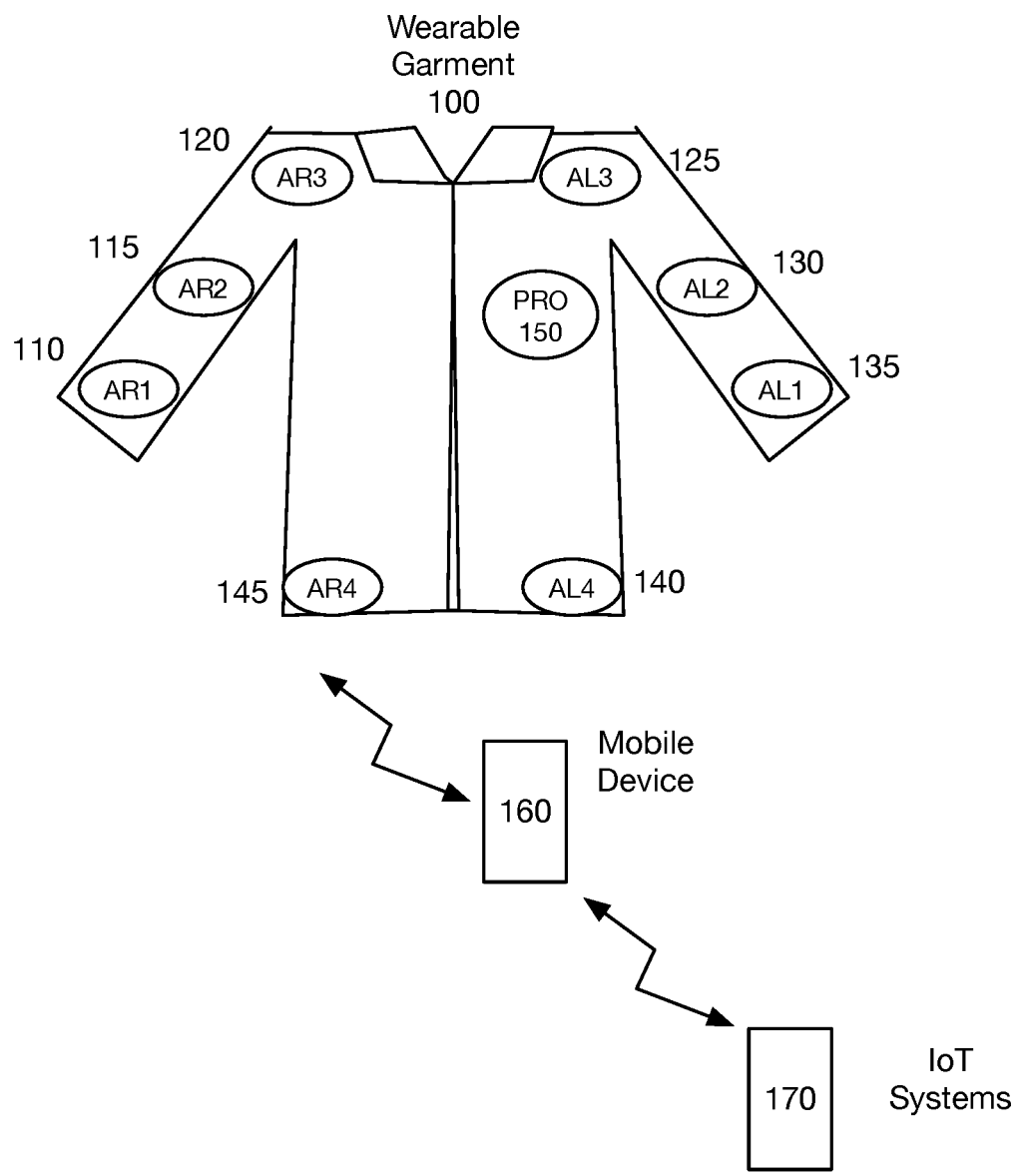
FIG. 1 is diagram showing an exemplary wearable, including a plurality of sensors.

FIG. 1 is diagram showing an exemplary wearable, including a plurality of sensors. In one embodiment, the wearable garment 100 includes a plurality of sensors 110 through 145. In one embodiment, the sensors are distributed through the garment 100. In one embodiment, the garment 100 is a jacket. In one embodiment, for a jacket, the sensors are distributed along both arms (right and left) and at the user's hips. This enables the system to monitor the user's motions closely. In one embodiment a subset of such sensors may be present in a garment 100. For example, the subset of sensors may include a sensor along each arm, and a sensor in one position on a hip. Alternate sets of sensors may be used. In one embodiment, the sensors may include one or more accelerometers, gyroscopes, and/or other motion sensors. The sensors may include temperature sensors, barometric sensors, microphones, and other environmental sensors as well. In one embodiment, other biometric sensors such as heart rate sensors may also be included. Additionally, other sensors which can obtain data about the user, or his or her environment may be included in garment 100.

In one embodiment, the garment 100 includes a processor and assorted other structures, PRO 150. The processor enables the garment to be intelligent and to process the sensor data. In one embodiment, the PRO 150 also includes memory and other elements that enable the wearable garment 100 to be intelligent. In one embodiment, the PRO 150 also includes communication mechanism that enables the wearable garment 100 to communicate with mobile device 160. Mobile device 160 in one embodiment is a smart phone, tablet, or other device which has network access and processing capability. In on embodiment, the wearable garment 100 utilizes low power Bluetooth (BLE)® for connection to mobile device 160. In one embodiment, the wearable garment 100 may also be coupled directly to IoT systems 170.

Mobile device 160 in one embodiment, receives raw sensor data from wearable garment 100. In one embodiment, mobile device 160 receives processed sensor data. In one embodiment, mobile device 160 also includes sensors, and the system integrates data from sensors in wearable garment 100 and mobile device 160 for making its determination. In one embodiment, an application on mobile device 160, or another computer system (not shown) may be used to configure and control the wearable garment 100.

Mobile device 160 in one embodiment communicates with IoT (Internet of Things) systems 170. The IoT systems 170 may control one or more aspects of the user's environment. In a vehicle, this may include the temperature, light levels, sounds, and in one embodiment navigation. Navigation may provide guidance to a safe resting location, when the systems indicate that the user is too drowsy to safely drive. In one embodiment, a safe resting location may provide a place to sleep in the vehicle, sleep outside the vehicle, walk around or exercise, or otherwise recover from the drowsiness.

In one embodiment, the system may also connect to a server (not shown). The server may provide processing power. In one embodiment, the server may further provide analytics to adjust the factors utilized by garment 100 and/or mobile device 160 to identify potential drowsiness. In one embodiment, sensor data and analytics may be split between the garment 100, mobile device 160, IoT systems 170, and server.

Figure 2:
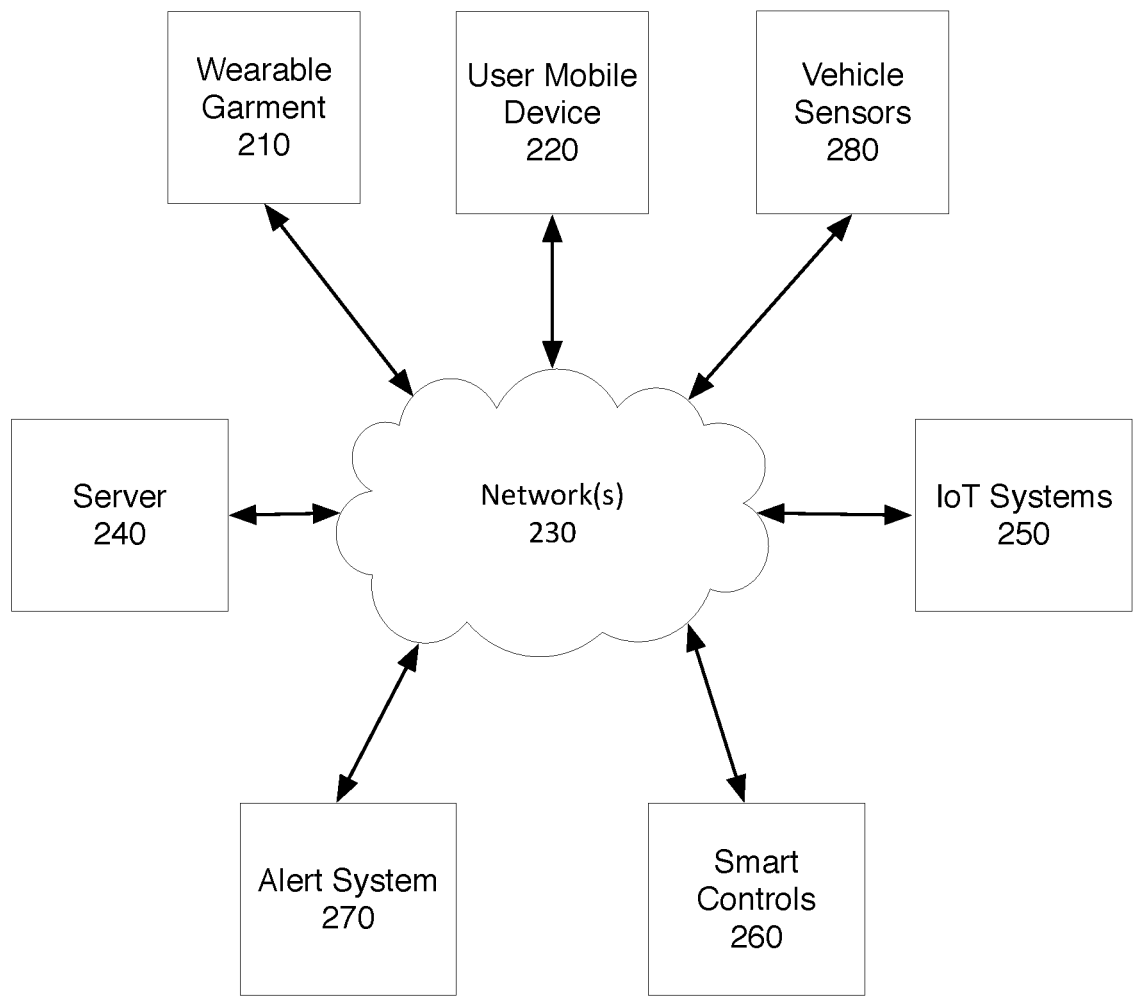
FIG. 2 is a network diagram showing the elements of one embodiment of the system.

FIG. 2 is a network diagram showing the elements of one embodiment of the system. Wearable garment 210 is coupled to network 230. In one embodiment, this network connection is an area network, such as a low power BLE (Bluetooth Low Energy) connection. In one embodiment, the wearable garment 210 is coupled via the network connection to a user mobile device 220. User mobile device 220 may coupled to server 240, via a network. In this example, the network 230 may be a cellular network connection, a wireless/Wi-Fi connection, or another type of connection. In one embodiment, the user mobile device 220 and/or wearable garment 210 may connect to IoT systems 250. IoT systems may be in a vehicle, enabling the mobile device 220 and/or garment 210 to control the environment within the vehicle or other area.

In one embodiment, the system also utilizes vehicle sensors 280, to monitor the user's behavior, which may be useful to detect fatigue precursors. For example, speed of acceleration, sudden breaking, the grip of the steering wheel of there is a pressure sensitive steering wheel available, and other aspects of the user's interaction with the vehicle. In one embodiment, the vehicle sensor data is sent via a network 230 or a physical connection to the mobile device 220 or wearable garment 210, for the integrated analysis. Other sensors, for example, a wristband, smart watch, smart seat, or other system which monitors the user's biometric or motion data may also provide information for analysis. In one embodiment, the system integrates data from all available sensors, to make its determination of potential fatigue.

In one embodiment, smart controls 260 are used in a system that does not include IoT but rather permits remote control of certain controls within the vehicle. This may be done, in one embodiment, via a remote connection, such as OnStar, with which the mobile device 220 interacts. In this way, the system may be able to control the environment in a non-IoT vehicle.

In one embodiment, alert system 270 may be utilized to alert user to a potential risk issue, such as drowsiness. In one embodiment, alert system 270 may include controls of the vehicle's notification mechanism including lights, horn, radio, and other output features.

Figure 3A:
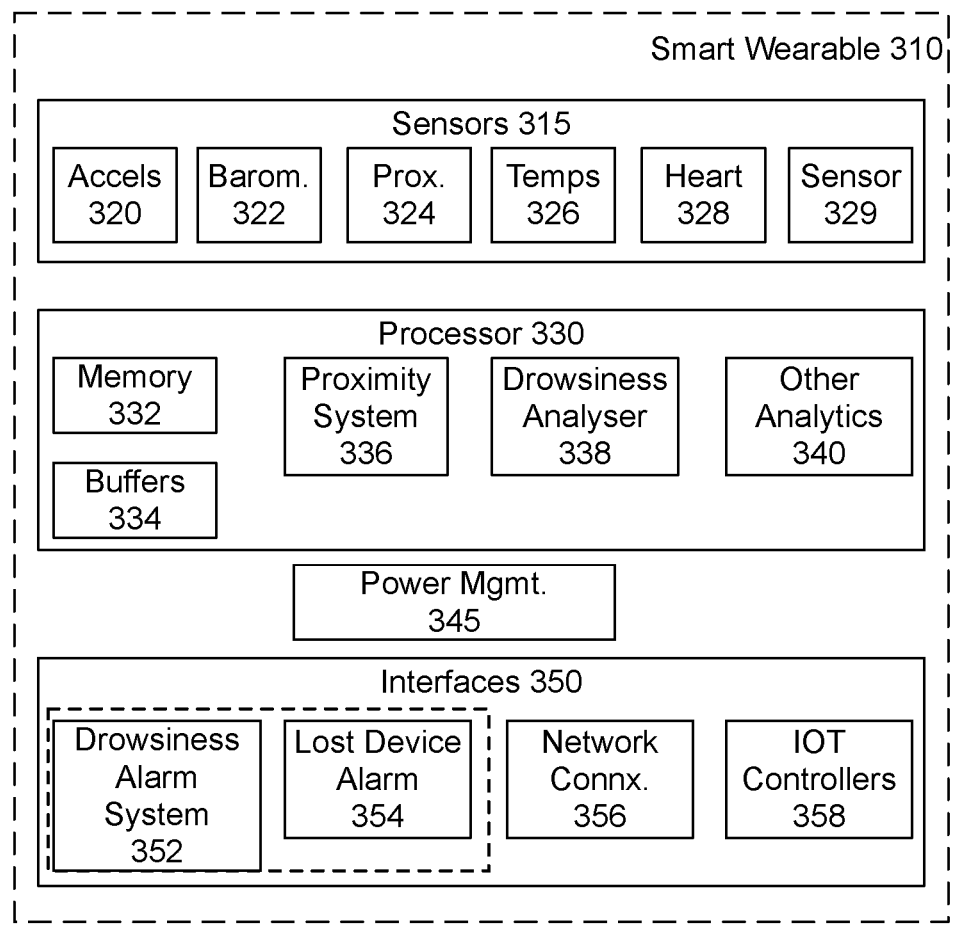
FIG. 3A is a block diagram of one embodiment of a wearable.

FIG. 3A is a block diagram of one embodiment of a wearable. The wearable 310 includes one or more of a plurality of sensors 315, a processor 330, and interfaces 350. Interfaces 350 may include the notifications to alert the user, as well as network connections, and IoT controllers 358. In one embodiment, the wearable may include a subset of these elements. At a minimum, the wearable 310 includes at least one sensor and a network connection 356 that enables the sensor data to be sent to a mobile device for processing. At a maximum, the wearable garment 310 may be a stand-alone system that directly controls IoT systems, in a vehicle or other environment, without the use of a mobile device, utilizing network connection 356.

The sensors 315 of the wearable 310 may include acceleration 320, barometric pressure 322, proximity sensor 324, temperature sensors 326, heart rate sensor 328, and other sensors 329. In one embodiment, temperature sensors 326 may include a body temperature and an environmental temperature sensor.

Processor 330 in one embodiment includes memory 332, buffers 334, as well as drowsiness analyzer 338 and other analytics 340. In one embodiment, processor 330 also includes proximity system 336 which utilizes the connection with the mobile device to ensure that the wearable 310 is not lost, or left behind. In one embodiment, the proximity system 336 is smart, and is able to distinguish between being left on the coat rack at home v. being left in a car or coffee shop, as will be described below.

In one embodiment, wearable 310 includes power management system 345, which controls the power to the elements of the wearable 310. In one embodiment, power management system 345 may place the processor 330 in a low power mode when the wearable 310 is not being used. In one embodiment, when the wearable 310 is not used, the sensors 315 are placed in a low power mode, or turned off, except for one sensor used to trigger the power management 345. In one embodiment, the low power sensor may be an accelerometer or proximity sensor. In one embodiment, the power management system 345 may also turn off interfaces 350 when the wearable 310 is not in use. This enables the wearable 310 to maintain power for an extended period, without requiring charging.

In one embodiment, wearable 310 includes a plurality of interfaces 350, to communicate to other devices and to the user. In one embodiment, interfaces 350 may include an alarm system 351 which may include a vibration and/or sound based alarm for drowsiness 352 and lost device 354. In one embodiment, there may also be a medical alarm, in alarm system 351. In one embodiment, interfaces 350 also include a network connection 356, which is a low power connection, such as Bluetooth BLE. In one embodiment, wearable 310 may include IoT controllers 358, enabling the wearable 310 to directly send commands, or receive commands, in an IoT setting. In one embodiment, the IoT controllers 358 may be configurable, based on the use of the wearable 310. For example, if a user has an IoT enabled vehicle, the user may configure the wearable 310 to provide updates to navigation, or receive alerts if the vehicle sensors detect drowsiness. In one embodiment, the wearable 310 may be configured for interface with the various types of IoT controllers 358.

Figure 3B:
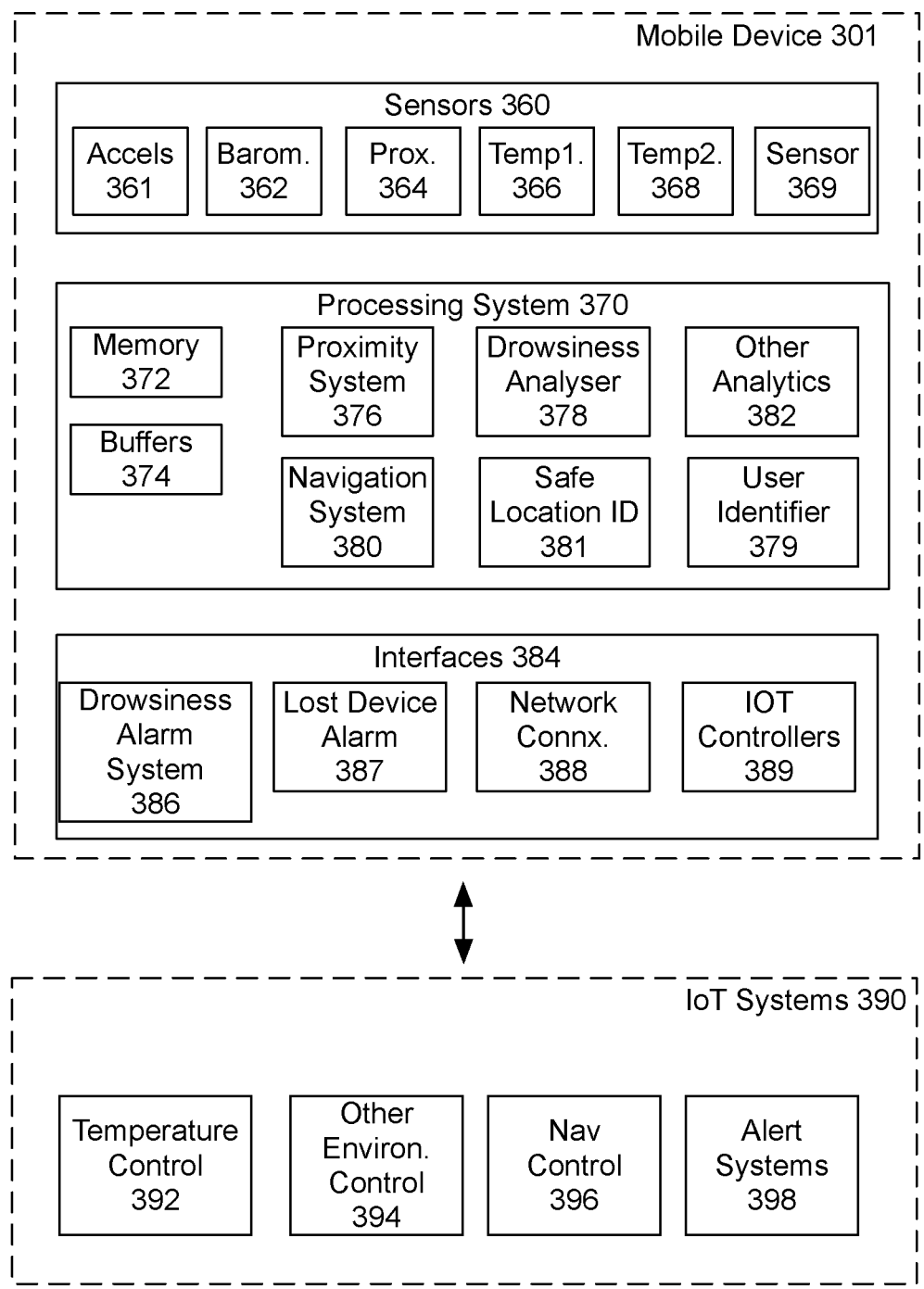
FIG. 3B is a block diagram of on embodiment of a mobile device and IoT controllers.

FIG. 3B is a block diagram of on embodiment of a mobile device and IoT controllers. The mobile device 301 may include one or more sensors 360, processor 370 and associated elements, and interfaces 384. The mobile device 301 may be excluded from the system entirely, in one embodiment. The mobile device 301 may provide all of the processing in another embodiment. Other configurations may be utilized.

The mobile device sensors 360 may include acceleration sensors 361, barometric sensors 352, proximity sensors 364, temperature sensors (366/368), and other sensors 369.

Processing system 370 may include memory 372 and buffers 374, as well as analytics including proximity system 376, navigation system 380, drowsiness analyzer 378, and other analytics 382. In one embodiment, the processing system 370 may receive data from sensor 360 and from wearable 310, and combine the data for processing. This enables more complete data. Proximity system 376 utilizes the network connection between mobile device 301 and wearable 310 to determine whether the wearable 310 or mobile device 301 have been left behind. In one embodiment, the mobile device 301 includes safe location ID 381, which enables the system to determine whether the wearable 310 has been left behind in a restaurant or car, or just hung up at home or in the office. In one embodiment, the safe location ID 381 utilizes location data to determine whether the left-behind device is in a safe location. In one embodiment, motion data may be used for this determination.

In one embodiment, when the devices are separating, and both devices are moving, the user identifier 379 can utilize the data from the sensors to determine which device is being carried by the user, and which by a third party. In one embodiment, both the wearable 310 and mobile device 301 may include user identifier logic. In one embodiment, a gait pattern and speed is used to identify a user. In one embodiment, other detected or derived biometric data, such as heart rate, respiration, etc. may be used to identify the user.

The mobile device 301 also includes interfaces 384, which may include alarm systems, network connection 388, and IoT controllers 389. In one embodiment, some or all of these elements may be provided through the wearable 301 or IoT system 390.

The mobile device 301 communicates with IoT systems 390. In one embodiment, the wearable garment 300 communicates directly with IoT systems 390. Mobile device 301 and/or IoT systems 390 may also communicate with the server (not shown). IoT systems 390 include any aspects which may be controlled by wearable garment 310 or mobile device 301, to change the environment or circumstances of the user. It may include temperature control 392, other environmental controls 394 (such as air quality, sound, and light levels), navigation control 396, and alert systems 398 (which may include sound, light, etc.)

Figure 4:
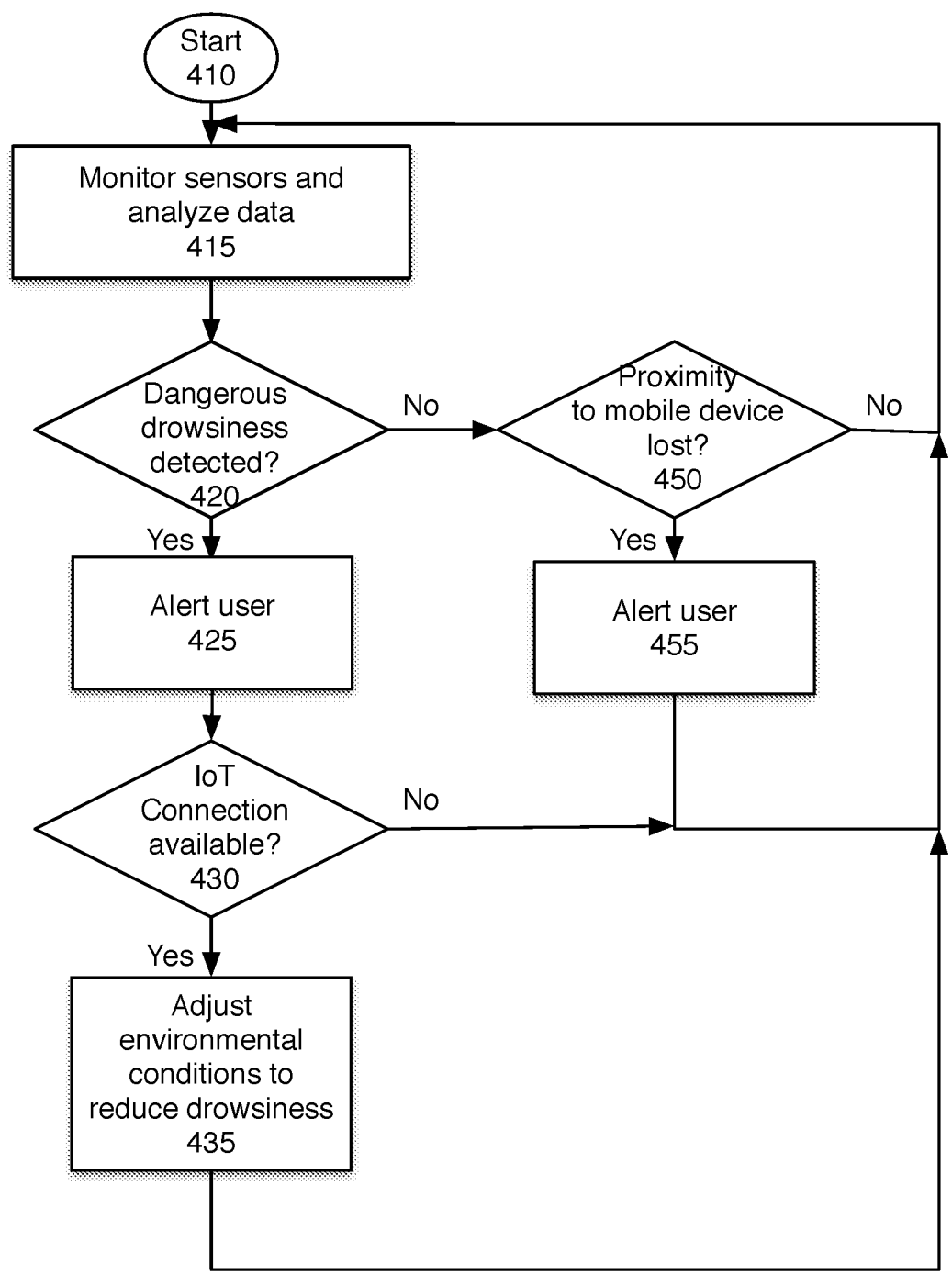
FIG. 4 is an overview flowchart of one embodiment of the system.

FIG. 4 is an overview flowchart of one embodiment of the system. The process starts at block 410. In one embodiment, the process starts when the user is wearing the wearable garment, and in the environment controlled by the IoT systems, such as a vehicle.

The sensors are monitored, and data is analyzed at block 415. The sensor data may include data from the wearable garment and/or mobile device.

At block 420, the process determines whether dangerous drowsiness is detected. Dangerous drowsiness is drowsiness when the user is performing an activity during which it would be dangerous to be excessively tired, such as driving. If no dangerous drowsiness is detected, the process determines at block 450 if the proximity to mobile device has been lost. If not, the system continues to monitor the sensors and analyze the sensor data.

If proximity is lost, at block 455, the user is alerted to the loss. In one embodiment, this enables the user to not lose the mobile device or the wearable garment. The process then returns to block 415 to continue monitoring.

If dangerous drowsiness is detected, at block 420, at block 425 the user is alerted.

At block 430, the system determines whether an IoT connection is available. An IoT connection, in this context is defined as the ability to control the user's environment in any way.

If an IoT connection is available, the user's environment is adjusted to reduce drowsiness. This may include adjusting the temperature, light levels, air blowing, windows, etc. The process then returns to block 415 to continue monitoring.

Of course, though this is shown as a flowchart, in one embodiment it is implemented as an interrupt-driven system, such that proximity and drowsiness are continuously monitored, and are triggered by detection, rather than a flowchart-chart type of sequential checking. Accordingly, the ordering of these checks is arbitrary.

Figure 5:
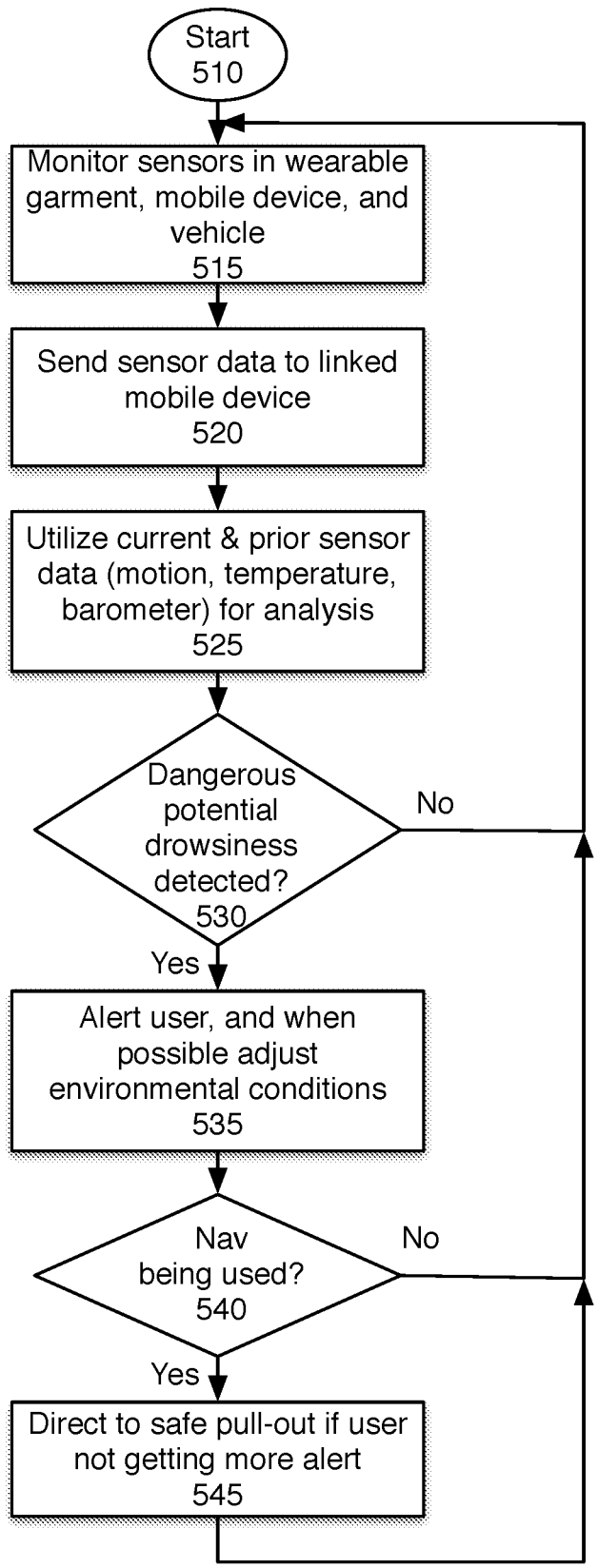
FIG. 5 is a flowchart of one embodiment of responding to user drowsiness using a connected wearable and mobile device.

FIG. 5 is a flowchart of one embodiment of responding to user drowsiness using a connected wearable and mobile device. Though this is specifically described with respect to drowsiness, one of skill in the art would understand that these techniques are applicable to other types of potentially dangerous behaviors or conditions. The process starts at block 510. In one embodiment, the sensors are monitored, in the wearable garment, mobile device, and vehicle.

At block 520, the sensor data is sent to the linked mobile device 520. In one embodiment, the sensor data is pre-processed by the wearable garment, prior to being passed to the mobile device. In another embodiment, the raw data is passed. In another embodiment, the results of the analysis are passed to the mobile device.

At block 525, the current and prior sensor data is used for analysis to determine whether the user is getting drowsy, or showing any precursors to dozing off.

The analysis may be designed to detect body motion patterns, which show signs or patterns of fatigue. The position of the user's arms and torso and neck for example, may be used. The analysis may be designed to detect posture, utilizing the plurality of sensors in the wearable. As people fatigue, they will often slouch, or lean off to a side.

The analysis may be designed to detect biometrics, such as body temperature, heart rate, respiration rate. For example heart rate and respiration rate will decrease as person gets fatigued. These metrics can be monitored by the wearable garment itself, and/or other wearables such as wrist bands/watches, or the car seat itself and sent to the jacket/smartphone.

The analysis may be designed to also utilize data received from the vehicle, if the vehicle is equipped with appropriate sensors. Such sensors, in one embodiment may monitor the users inputs to the car (steering, brake, accelerator, etc.) and car's behavior (changes in speed). The analysis of this data may be used to identify signposts of fatigue. For example, as the person becomes drowsy their speed stops being uniform, and their steering becomes more jerky. The system can integrate this car data, when it is available. In some embodiments, the steering wheel may have pressure/force sensitive sensors to monitor the user's grip.

At block 530, the processor determines whether potentially dangerous drowsiness is detected. In one embodiment, the system first determines whether the user is performing an activity that could be dangerous if the user dozed off. In one embodiment, if the user is not in a situation where dozing off may be dangerous, the system may turn off monitoring, to save power. In one embodiment, therefore, this process is only active when the user is in a situation where drowsing off would be dangerous.

If no dangerous potential drowsiness is detected, at block 530, the process continues to block 515, to continue monitoring the sensors. In one embodiment, because the sensor data is collected, the system may be used for other analytics as well. For example, user motion and temperature data may be used for monitoring for health conditions as well. For example, the system may detect a heart attack, stroke, seizure or other medical emergency. In one embodiment, the system may alert the user, and adjust environmental conditions. Additionally, if a medical emergency is detected, the system may further alert others locally (utilizing for example the car horn) or remotely (utilizing the mobile device to make an emergency call.)

At block 535, the user is alerted, and when possible the system alerts the environmental conditions. In one embodiment, the air conditioning is adjusted to blow air at the user, which increases wakefulness. Other adjustments, including for example lowering the window, turning on or adjusting the radio or other sound output mechanism, turning on a light, may be taken, in one embodiment.

At block 540, the process determines whether the user is using navigation. If not, the process returns to block 515, to continue monitoring.

If the user is utilizing the navigation system, whether through the user's mobile device or through the vehicle, the system may direct the user to a safe pull-out location, if the user does not stop being drowsy after the alert and adjustments made, at block 535. In one embodiment, if the vehicle has some self-driving features, the system may engage those features as well.

This may enable the user to safely exit the freeway, for example, when too tired to drive safely. A safe pull-out location may be a place the user could walk around, get something to drink, or take a nap. In one embodiment, when the system determines that the user is again alert, the navigation system is reset, to send the user on his or her way, to the original destination. The process then returns to block 515, to continue monitoring the sensors. In one embodiment, the system terminates when the user is no longer in an environment where the monitoring is no longer relevant.

Figure 6:
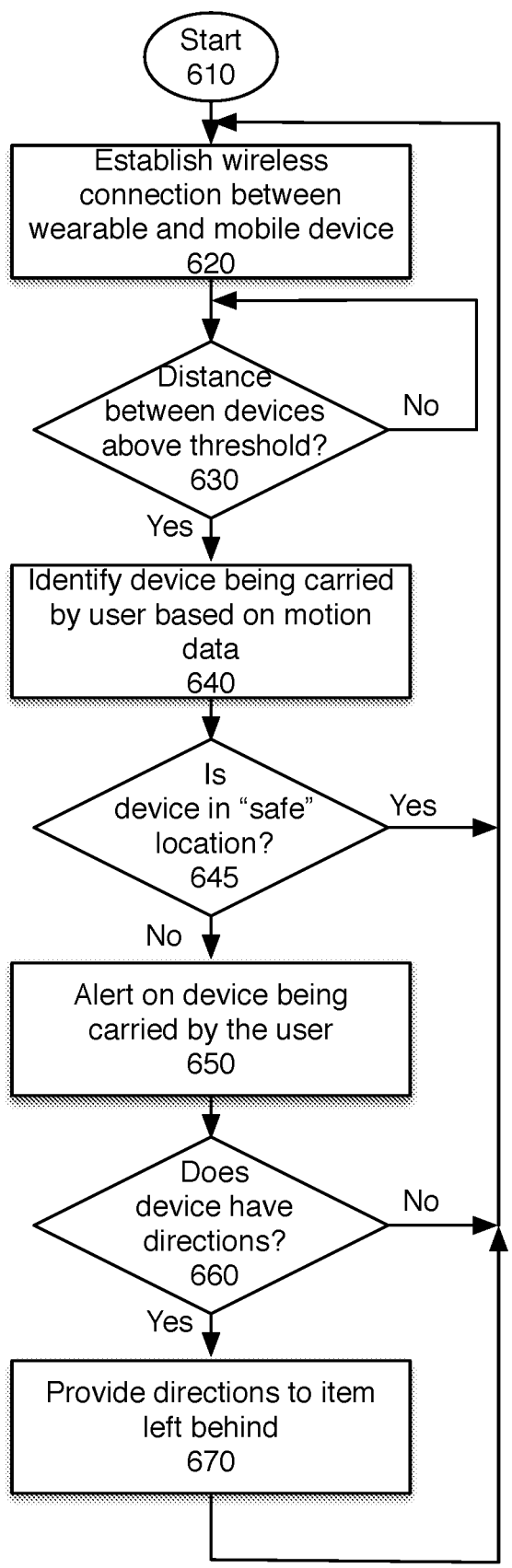
FIG. 6 is a flowchart of one embodiment of alerting a user to a lost wearable or device.

FIG. 6 is a flowchart of one embodiment of alerting a user to a lost wearable or device. The process starts at block 610.

At block 620, a wireless connection is established between the wearable and the mobile device. In one embodiment, this is done when the application is initiated.

At block 630, the process determines whether the distance between the devices is above a threshold. In one embodiment, this is done by timing signal lag between the devices. In on embodiment, the wearable provides data to the mobile device on a regular basis. In one embodiment, the proximity system of BLE may be used to make this determination. If the distance is not above the threshold, the process returns to block 630 to continue monitoring.

If the distance is above the threshold, at block 640 the device being carried by the user is identified based on motion data. In one embodiment, when a device is left behind it stops moving, in general. This may be used to determine which device remains with the user.

In one embodiment, if both devices are being carried, but still moving in separate directions, motion analysis may be used to identify which device is carried by the actual user, rather than a third party. In one embodiment, the sensor analysis can identify the particular user based on motion pattern, such as gait pattern and speed. In one embodiment, when someone other than the regular user picks up the wearable or the device, the system may provide an immediate alert.

At block 645, the process determines whether the left-behind device (whether mobile device or wearable) is in a safe location. In one embodiment, the mobile device's location system determines whether the location is the user's home, office, or another known safe location where the user is known to spend time. In one embodiment, the safe location may include the user's vehicle. In one embodiment, the vehicle location is identified based on data from the vehicle. In one embodiment, the vehicle location is identified based on recognizing the driving speed and pattern of the user. If the device is being left behind in a safe place, the system may not alert. In one embodiment, the system may store the location of the left-behind device.

At block 650, an alert is sounded on the device being carried by the user. At block 660, the process determines whether the device being carried can provide directions. If so, at block 670, the user is provided directions to the item left behind. The process then returns to block 620, to re-establish the wireless connection between the wearable and the mobile device. In one embodiment, if the wearable device is the one left behind, the wearable device may be powered down, to reduce power consumption.

Figure 7:
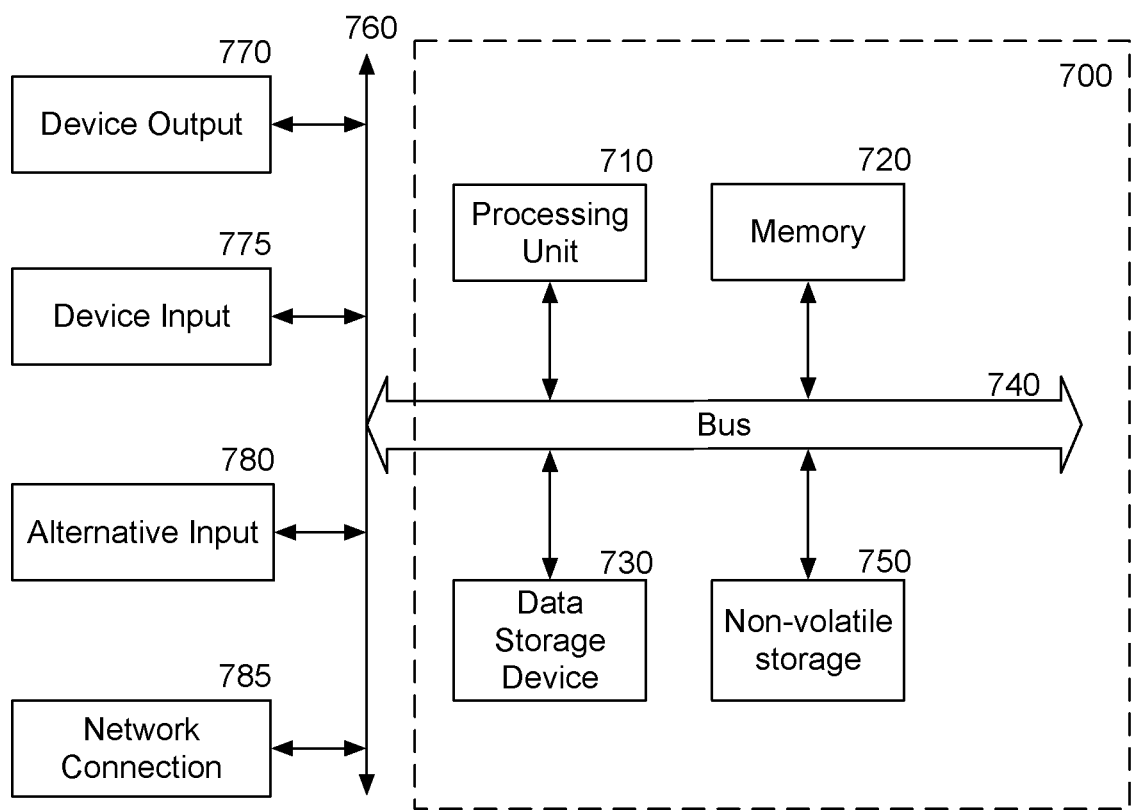
FIG. 7 is a block diagram of one embodiment of a computer system which may be used with the present invention.

FIG. 7 is a block diagram of one embodiment of a computer system that may be used with the present invention. It will be apparent to those of ordinary skill in the art, however that other alternative systems of various system architectures may also be used.

The data processing system illustrated in FIG. 7 includes a bus or other internal communication means 740 for communicating information, and a processing unit 710 coupled to the bus 740 for processing information. The processing unit 710 may be a central processing unit (CPU), a digital signal processor (DSP), a field programmable gate array (FPGA), or another type of processing unit 710. In one embodiment, for the wearable garment, the processing unit 710 is a low power processing unit, which is configured to minimize power consumption.

The system further includes, in one embodiment, a random access memory (RAM) or other volatile storage device 720 (referred to as memory), coupled to bus 740 for storing information and instructions to be executed by processor 710. Main memory 720 may also be used for storing temporary variables or other intermediate information during execution of instructions by processing unit 710.

The system also comprises in one embodiment a read only memory (ROM) 750 and/or static storage device 750 coupled to bus 740 for storing static information and instructions for processor 710. In one embodiment, the system also includes a data storage device 730 such as a magnetic disk or optical disk and its corresponding disk drive, or Flash memory or other storage which is capable of storing data when no power is supplied to the system. Data storage device 730 in one embodiment is coupled to bus 740 for storing information and instructions. In one embodiment, for the wearable garment, the data storage may be a flash memory or other static memory which is not sensitive to the movements and likely dropping and shaking experienced by a garment. In one embodiment, for the mobile device, the memory may also be a flash memory. In one embodiment, there may be a buffer, which is flash memory or RAM.

The system may further be coupled to an output device 770, such as a liquid crystal display (LCD) or one or more LEDs or other visual output mechanisms, coupled to bus 740 through bus 760 for outputting information. The output device 770 may be a visual output device, an audio output device, and/or tactile output device (e.g. vibrations, etc.) The wearable garment in one embodiment includes an audio output, to sound alerts. In one embodiment, the wearable garment may include alternatively or in addition, a haptic feedback mechanism. However, in one embodiment, the wearable garment does not include a visual output.

An input device 775 may be coupled to the bus 760. The input device 775 may be an alphanumeric input device, such as a keyboard (or virtual keyboard) including alphanumeric and other keys, for enabling a user to communicate information and command selections to processing unit 710. An additional user input device 780 may further be included. One such user input device 780 is cursor control device 780, such as a mouse, a trackball, stylus, cursor direction keys, or touch screen, may be coupled to bus 740 through bus 760 for communicating direction information and command selections to processing unit 710, and for controlling movement on display device 770. The wearable device, in one embodiment, may not have any direct input mechanisms. Rather, it may be controlled through an application, which may run on the associated mobile device or the user's computer system. This enables a wearable device with very limited user interface elements to perform complex interactions.

Another device, which may coupled to computer system 700, is a network device 785 for accessing other nodes of a distributed system via a network. The communication device 785 may include any of a number of commercially available networking peripheral devices such as those used for coupling to an Ethernet, token ring, Internet, or wide area network, personal area network, wireless network or other method of accessing other devices. The communication device 785 may further be a null-modem connection, or any other mechanism that provides connectivity between the computer system 700 and the outside world. In one embodiment, in the wearable device, the network is a low power local area network, such as low bluer Bluetooth.

Note that any or all of the components of this system illustrated in FIG. 7 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 720, mass storage device 730, or other storage medium locally or remotely accessible to processor 710.

It will be apparent to those of ordinary skill in the art that the system, method, and process described herein can be implemented as software stored in main memory 720 or read only memory 750 and executed by processor 710. This control logic or software may also be resident on an article of manufacture comprising a computer readable medium having computer readable program code embodied therein and being readable by the mass storage device 730 and for causing the processor 710 to operate in accordance with the methods and teachings herein.

The present invention may also be embodied in a handheld or portable device containing a subset of the computer hardware components described above. For example, the handheld device may be configured to contain only the bus 740, the processor 710, and memory 750 and/or 720.

The handheld device may be configured to include a set of buttons or input signaling components with which a user may select from a set of available options. These could be considered input device #1 775 or input device #2 780. The handheld device may also be configured to include an output device 770 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 710, a data storage device 730, a bus 740, and memory 720, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 785.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 710. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A system comprising:
   a wearable garment including a plurality of sensors to monitor a user, while the user is driving a vehicle, and a capability to communicate with other devices;
   a mobile device in communication with the wearable garment, the mobile device and the wearable garment determining a user's condition in the vehicle;
   an alarm that alerts the user when the user's determined condition is a precursor to the user dozing off in the vehicle;
   an IoT environment controlled on the basis of the determining, the IoT environment automatically adjusting one or more environmental conditions to keep the user from dozing off in the vehicle, the IoT environment controlled in addition to the alarm;
   a navigation system to automatically redirect the user in the vehicle to a safe resting location when one of the alarm and the adjusting the one or more environmental conditions is insufficient to rouse the user from drowsiness while the user is in the vehicle;

a proximity system in the mobile device and the wearable device, to detect when one of the mobile device and the wearable device are left behind, and the other device remaining with the user to alert the user; and a safe location identification to enable determination of whether the wearable garment is being left behind in a location, and to alert when the location is not a safe location.

2. The system of claim 1, wherein the IoT environment comprises a vehicle, and the environmental conditions comprise one or more of temperature and navigation.

3. The system of claim 2, wherein the navigation comprises:

the IoT environment instructing a guidance logic to navigate the vehicle to the safe resting location.

4. The system of claim 1, wherein the safe location includes at least: home, office, and in a user's vehicle.

5. The system of claim 1, wherein the wearable garment is a jacket.

6. The system of claim 5, wherein the jacket comprises:

a plurality of sensors positioned in a plurality of locations on the jacket; and a processor and other structures (PRO) to collect data from the plurality of sensors and enable the jacket to communicate with external systems.

7. The system of claim 6, wherein the plurality of sensors include one or more of: a motion sensor, a heart rate sensor, a blood pressure sensor, and a temperature sensor.

8. The system of claim 1, further comprising:

the mobile device to interface with the wearable garment, the mobile device further to interface with the IoT environment.

9. The system of claim 1, wherein the sensors in the wearable garment are further capable of detecting a medical emergency.

10. A method comprising:

monitoring sensors in a wearable garment worn by a user, while the user is driving a vehicle, the wearable garment having a capability to communicate with other devices;

communicating, by the wearable garment with a mobile device, the mobile device and the wearable garment determining a user's condition in the vehicle;

alerting the user when the user's determined condition is a precursor to dozing off in the vehicle;

controlling an IoT environment on the basis of the determining, the IoT environment automatically adjusting one or more environmental conditions to keep the user from dozing off in the vehicle, the IoT environment controlled in addition to the alarm;

automatically redirecting the user in the vehicle to a safe resting location when one of the alerting the user and the adjusting the one or more environmental conditions is insufficient to rouse the user from drowsiness in the vehicle;

a proximity system in the mobile device and the wearable device, to detect when one of the mobile device and the wearable device are left behind, and the other device remaining with the user to alert the user; and determining whether the wearable garment is being left behind in a location and sending an alert when the location is not a safe location.

11. The method of claim 10, wherein the wearable garment is a jacket.

12. The method of claim 11, wherein the jacket comprises:

a plurality of sensors positioned in a plurality of locations on the jacket; and a processor and other structures (PRO) to collect data from the plurality of sensors and enable the jacket to communicate with external systems.

13. The method of claim 10, wherein the IoT environment comprises a vehicle, and the environmental conditions comprise one or more of temperature and navigation.

14. The method of claim 13, wherein the navigation comprises:

instructing a guidance logic in the IoT environment to navigate the vehicle to a safe resting location.

15. The system of claim 1, wherein the IoT environment is controlled to ensure that the user stays awake.

16. The method of claim 10, wherein the IoT environment is controlled to ensure that the user stays awake.

17. The system of claim 1, wherein the navigation system is reset to navigate to the user's original destination, when the user is determined to be alert again.

18. The method of claim 14, wherein the navigation is reset to navigate to the user's original destination, when the user is determined to be alert again.

* * * * *